United States Patent

Iizuka

(10) Patent No.: US 9,277,891 B2
(45) Date of Patent: Mar. 8, 2016

(54) IMAGE DIAGNOSIS ASSISTANCE APPARATUS, PROCESSING METHOD THEREOF, AND STORAGE MEDIUM

(71) Applicant: CANON KABUSHIKI KAISHA, Tokyo (JP)

(72) Inventor: Yoshio Iizuka, Kyoto (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 254 days.

(21) Appl. No.: 13/744,835

(22) Filed: Jan. 18, 2013

(65) Prior Publication Data

US 2013/0190593 A1    Jul. 25, 2013

(30) Foreign Application Priority Data

Jan. 24, 2012   (JP) ................................ 2012-012433

(51) Int. Cl.
| | |
|---|---|
| *G06K 9/00* | (2006.01) |
| *A61B 5/00* | (2006.01) |
| *G06F 19/00* | (2011.01) |
| *G06T 7/00* | (2006.01) |

(52) U.S. Cl.
CPC ............ *A61B 5/7282* (2013.01); *A61B 5/0013* (2013.01); *A61B 5/7225* (2013.01); *A61B 5/742* (2013.01); *A61B 5/7475* (2013.01); *G06F 19/345* (2013.01); *G06T 7/0014* (2013.01); *G06T 2207/20081* (2013.01); *G06T 2207/30068* (2013.01)

(58) Field of Classification Search
USPC ................................................. 382/128–134
See application file for complete search history.

(56) References Cited

U.S. PATENT DOCUMENTS

| | | | | |
|---|---|---|---|---|
| 5,807,256 | A * | 9/1998 | Taguchi et al. ............... | 600/425 |
| 5,825,936 | A * | 10/1998 | Clarke et al. .................. | 382/261 |
| 6,778,692 | B1* | 8/2004 | Yazici ............................ | 382/132 |
| 2007/0014454 | A1* | 1/2007 | Sawyer et al. ................ | 382/128 |
| 2007/0016373 | A1* | 1/2007 | Hunter et al. .................... | 702/19 |
| 2008/0240338 | A1* | 10/2008 | Boese et al. ....................... | 378/4 |
| 2008/0240494 | A1* | 10/2008 | Oosawa et al. ............... | 382/100 |
| 2008/0247618 | A1* | 10/2008 | Laine et al. ................... | 382/128 |
| 2011/0246410 | A1* | 10/2011 | Iizuka et al. .................... | 706/52 |

FOREIGN PATENT DOCUMENTS

| | | |
|---|---|---|
| JP | 2006-163465 A | 6/2006 |
| JP | 2008-541889 A | 11/2008 |
| JP | 2009-082441 A | 4/2009 |
| JP | 2010-200840 A | 9/2010 |
| WO | 2006/128302 A | 12/2006 |

OTHER PUBLICATIONS

Japanese Office Action issued in corresponding application No. 2012-012433 on Sep. 7, 2015.

* cited by examiner

*Primary Examiner* — Alex Liew
(74) *Attorney, Agent, or Firm* — Carter, DeLuca, Farrell & Schmidt, LLP

(57) ABSTRACT

An image diagnosis assistance apparatus calculates a first characteristic value based on an image feature of an image that is a diagnosis target, acquires a second characteristic value based on the findings information of the image input by a user via an operation unit, and performs diagnostic inference for a predetermined region of the image based on the first characteristic value, the second characteristic value, and the reliability of inference of the first characteristic value and the second characteristic value.

21 Claims, 4 Drawing Sheets

FIG. 3

| i | $F1_i$ | $F2_i$ | RANGE OF $V1_i$ AND $V2_i$ |
|---|---|---|---|
| 1 | MAJOR AXIS | MAJOR AXIS | ≥ 1mm |
| 2 | IRREGULARITY OF CONTOUR | IRREGULARITY OF CONTOUR | 1~5 |
| 2 | CALCIFICATION | CALCIFICATION | 1~5 |
| 2 | GASEOUS PORTION | GASEOUS PORTION | 1~5 |
| ⋮ | ⋮ | ⋮ | ⋮ |
| p | VARIANCE OF DENSITIES | | ≥ 0 |
| ⋮ | ⋮ | ⋮ | ⋮ |
| q | | INVOLUTION OF BLOOD VESSELS | 1~5 |
| ⋮ | ⋮ | ⋮ | ⋮ |

FIG. 4

| i | $F1_i$ | $F2_i$ | $W1_i$ | $W2_i$ |
|---|---|---|---|---|
| 1 | MAJOR AXIS | MAJOR AXIS | 0.7 | 0.3 |
| 2 | IRREGULARITY OF CONTOUR | IRREGULARITY OF CONTOUR | 0.2 | 0.8 |
| 2 | CALCIFICATION | CALCIFICATION | 0.4 | 0.6 |
| 2 | GASEOUS PORTION | GASEOUS PORTION | 0.4 | 0.6 |
| ⋮ | ⋮ | ⋮ | ⋮ | ⋮ |
| p | VARIANCE OF DENSITIES | | 1.0 | 0.0 |
| ⋮ | ⋮ | ⋮ | ⋮ | ⋮ |
| q | | INVOLUTION OF BLOOD VESSELS | 0.0 | 1.0 |
| ⋮ | ⋮ | ⋮ | ⋮ | ⋮ | ured to perform diagnostic inference for the image based on the first characteristic value, the second characteristic value, and a reliability of inference of the first characteristic value and the second characteristic value.

According to one aspect of the present invention, there is provided a processing method of an image diagnosis assistance apparatus, comprising: calculating, by a first characteristic value calculation unit, a first characteristic value based on an image feature of an image that is a diagnosis target; acquiring, by a second characteristic value acquisition unit, a second characteristic value based on findings information of the image input by a user via an operation unit; and performing, by an inference unit, diagnostic inference for the image based on the first characteristic value, the second characteristic value, and a reliability of inference of the first characteristic value and the second characteristic value.

Further features of the present invention will be apparent from the following description of exemplary embodiments with reference to the attached drawings.

IMAGE DIAGNOSIS ASSISTANCE APPARATUS, PROCESSING METHOD THEREOF, AND STORAGE MEDIUM

BACKGROUND OF THE INVENTION

1. Field of the Invention

The present invention relates to an image diagnosis assistance apparatus, a processing method thereof, and a storage medium.

2. Description of the Related Art

One known data processing technology using a computer is inference technology, where an unknown event is inferred based on knowledge extracted from a known event. Even in the medical field, studies have recently been carried out to assist the diagnosis of a morbid portion using an inference apparatus. For example, research is being conducted to develop a technique of inputting the characteristic values (image features or image findings) of a medical image and inferring whether an abnormal shade on the medical image is benign or malignant.

Japanese Patent Laid-Open No. 2008-541889 discloses a system that analyzes a medical image, extracts image features, calculates initial diagnosis based on them, and offers the user the initial diagnosis. In this system, when the user changes the image features, the diagnosis result is dynamically recalculated. The thus calculated image features and diagnosis result are generated as a diagnosis report after the user has confirmed and properly modified.

Japanese Patent Laid-Open No. 2006-163465 discloses a technique of calculating and outputting the predicted value of a target variable value (for example, diagnosis) of input unknown medical data and the reliability measure of the prediction itself based on known medical data accumulated in a database.

In the above-described technique of Japanese Patent Laid-Open No. 2008-541889, the system performs image feature calculation and diagnoses before the user and presents the result to the user. For this reason, it is impossible to cause the user to input image features and a diagnosis result first and then cause the system to present, to the user, image features and diagnosis results calculated later. In the technique of Japanese Patent Laid-Open No. 2008-541889, if the user changes an image feature, the image feature calculated by the system is not used for the image feature. For this reason, even if the system can calculate a more reliable image feature than the user, it is not used, and more reliable diagnostic inference cannot be performed.

Japanese Patent Laid-Open No. 2006-163465 allows calculation of the predicted value of diagnosis and the reliability measure of the prediction itself. However, even if the reliability is revealed to be poor, more reliable diagnostic inference cannot be performed.

SUMMARY OF THE INVENTION

According to one aspect of the present invention, there is provided a technique of allowing obtainment of a diagnostic inference result more reliable than previously.

According to one aspect of the present invention, there is provided an image diagnosis assistance apparatus comprising: a first characteristic value calculation unit configured to calculate a first characteristic value based on an image feature of an image that is a diagnosis target; a second characteristic value acquisition unit configured to acquire a second characteristic value based on findings information of the image input by a user via an operation unit; and an inference unit config-

BRIEF DESCRIPTION OF THE DRAWINGS

FIG. 3 is a table showing detailed examples of a first characteristic value and a second characteristic value;

FIG. 4 is a table showing detailed examples of a first weight and a second weight for the first characteristic value and the second characteristic value.

DESCRIPTION OF THE EMBODIMENTS

An exemplary embodiment of the present invention will now be described in detail with reference to the drawings. It should be noted that the relative arrangement of the components, the numerical expressions and numerical values set forth in these embodiments do not limit the scope of the present invention unless it is specifically stated otherwise.

Figure 1:
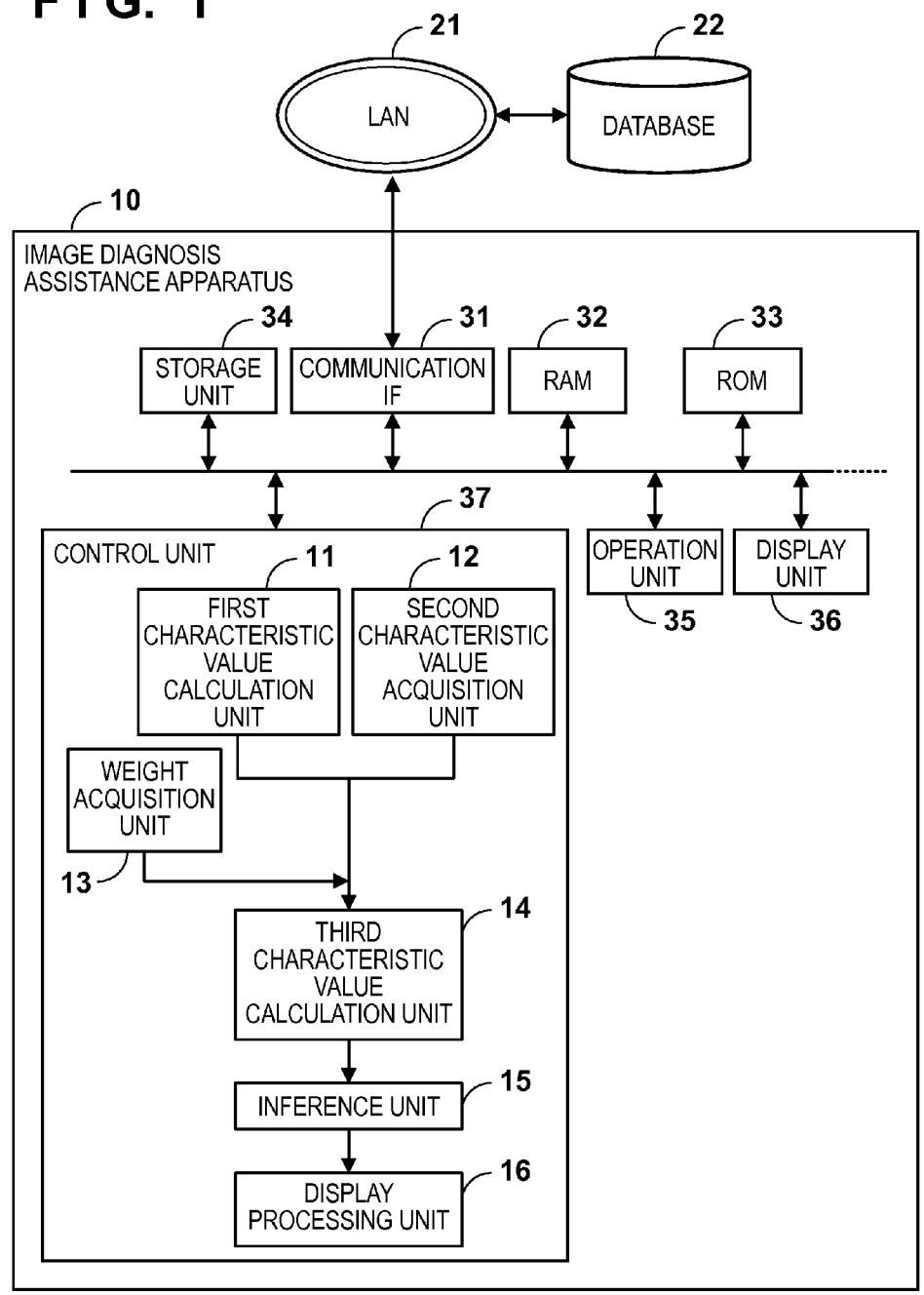
FIG. 1 is a block diagram showing an example of the overall arrangement of an image diagnosis assistance system including an image diagnosis assistance apparatus according to an embodiment of the present invention.

FIG. 1 is a block diagram showing an example of the overall arrangement of an image diagnosis assistance system including an image diagnosis assistance apparatus according to an embodiment of the present invention.

The image diagnosis assistance system includes an image diagnosis assistance apparatus 10 and a database 22. These apparatuses are communicably connected via a communication unit (in this case, LAN (Local Area Network) 21).

The database 22 manages medical images and information associated with them. The image diagnosis assistance apparatus 10 acquires, via the LAN 21, a medical image (diagnosis target image) that is a diagnosis target managed on the database 22 and information associated with it.

The image diagnosis assistance apparatus 10 includes, as its functional components, a communication IF (interface) 31, a RAM (Random Access Memory) 32, a ROM (Read Only Memory) 33, a storage unit 34, an operation unit 35, and a display unit 36.

The communication IF 31 is implemented by, for example, a LAN card and controls communication performed between an external apparatus (for example, the database 22) and the image diagnosis assistance apparatus 10 via the LAN 21. The storage unit 34 is implemented by, for example, an HDD (Hard Disk Drive) and stores various kinds of information.

The display unit 36 is implemented by, for example, a display and displays various kinds of information for the user (for example, doctor). The operation unit 35 is implemented by, for example, a keyboard and a mouse and inputs a user instruction to the apparatus.

The RAM 32 is implemented by a volatile memory or the like and temporarily stores various kinds of information. The ROM 33 is implemented by a nonvolatile memory or the like and stores various kinds of programs. A control unit 37 is implemented by, for example, a CPU (Central Processing Unit) and systematically controls processing in the image diagnosis assistance apparatus 10.

The control unit 37 includes, as its functional components, a first characteristic value calculation unit 11, a second characteristic value acquisition unit 12, a weight acquisition unit 13, a third characteristic value calculation unit 14, an inference unit 15, and a display processing unit 16. These components are implemented by, for example, causing the CPU to read out and execute programs stored in the ROM 33 or the like using the RAM 32 as a work area. Note that some or all of the components may be implemented by dedicated circuits.

The first characteristic value calculation unit 11 performs image processing for a predetermined region (abnormal shade region) of a diagnosis target image and thus calculates a characteristic value (first characteristic value). The second characteristic value acquisition unit 12 acquires an image finding (findings information) of the user (doctor) for the abnormal shade region of the diagnosis target image as a characteristic value (second characteristic value). This acquisition is done based on, for example, a user operation via the operation unit 35.

The weight acquisition unit 13 acquires a weight (first weight) for the first characteristic value and a weight (second weight) for the second characteristic value.

The third characteristic value calculation unit 14 calculates a new characteristic value (third characteristic value) using the first characteristic value, the second characteristic value, the first weight, and the second weight.

The inference unit 15 performs diagnostic inference for the abnormal shade of the diagnosis target image using the third characteristic value. The display processing unit 16 presents the user various kinds of information such as the diagnosis target image, the first characteristic value, the second characteristic value, and the diagnostic inference result. This presentation is done by, for example, displaying a screen on the display unit 36. The presentation may be done by printing using a printer or the like, as a matter of course.

An example of the procedure of processing of the image diagnosis assistance apparatus 10 shown in FIG. 1 will be described next with reference to FIG. 2.

When the user instructs, via the operation unit 35, to acquire a diagnosis target image managed on the database 22, the processing starts. When the processing starts, the image diagnosis assistance apparatus 10 acquires the diagnosis target image from the database 22 via the LAN 21 in accordance with the user instruction and stores it in the RAM 32 (step S101). The display processing unit 16 of the image diagnosis assistance apparatus 10 displays the diagnosis target image on the display unit 36. Note that the diagnosis target image may be acquired from an external storage device connected to the image diagnosis assistance apparatus 10.

The user designates an abnormal shade position on the diagnosis target image via the operation unit 35. The first characteristic value calculation unit 11 of the image diagnosis assistance apparatus 10 acquires the abnormal shade position in accordance with the user operation and specifies and acquires the abnormal shade region using a known region extraction technique (graph cuts method, level set method, or the like) (step S102). Note that the abnormal shade region may automatically be acquired using a known abnormal shade detection technique.

The first characteristic value calculation unit 11 of the image diagnosis assistance apparatus 10 calculates an image feature of the abnormal shade using a known image processing technique (step S103) and calculates a first characteristic value based on the image feature (step S104). Examples of the image feature are the shape features (major axis (maximum diameter), boundary circularity, oblateness, and irregularity) and density features (average and variance of densities, presence/absence and presence ratio of density values in a specific density range corresponding to calcification, air, or the like) of the abnormal shade region. Note that the method of calculating the first characteristic value will be described later.

When the first characteristic value is calculated, the user inputs an image finding via the operation unit 35. That is, the user who has referred to the diagnosis target image displayed on the display unit 36 by the processing in step S101 inputs the finding result of the abnormal shade on the image. The second characteristic value acquisition unit 12 of the image diagnosis assistance apparatus 10 directly acquires the image finding input in accordance with the user operation as a second characteristic value (step S105).

Note that examples of the image finding (second characteristic value) are the major axis (maximum diameter) of the abnormal shade, overall shape, and information about the presence/absence and degree of spine, irregularity of contour, calcification, gaseous portion, involution of blood vessels or bronchi, pleura inlay, bronchus hypertranslucency, and the like. Note that the processing in step S105 can be executed at the same time as the processes in steps S102 to S104 or before execution of the processes in steps S102 to S104.

FIG. 3 is a table showing detailed examples of the first characteristic value and the second characteristic value.

The table of FIG. 3 includes (p−1) (p≥2) characteristic values $F1_1$ to $F1_{p-1}$ or $F2_1$ to $F2_{p-1}$ commonly used as the first characteristic value and the second characteristic value.

The table also includes (q−p) (q>p) characteristic values $F1_p$ to $F1_{q-1}$ that exist only as the first characteristic value and (n−q+1) (n≥q) characteristic values $F2_q$ to $F2_n$ that exist only as the second characteristic value. However, the characteristic values that exist only as the first characteristic value or the characteristic values that exist only as the second characteristic value may be absent.

In the table of FIG. 3, i is the index of the first characteristic value and the second characteristic value, $F1_i$ is the ith first characteristic value, and $F2_i$ is the ith second characteristic value. In addition, values the individual characteristic values $F1_i$ and $F2_i$ can take are represented by $V1_i$ and $V2_i$, respectively.

As exemplified by the table of FIG. 3, the ranges of (values taken by) $V1_i$ and $V2_i$ change depending on the index i. For example, assume that the value $V1_i$ ranges from 1 to 5 for some characteristic values ($F1_2$ to $F1_4$). In this case, the closer to 1 the value $V1_i$ is, the less (smaller or weaker) the characteristic represented by the characteristic value $F1_i$ is. The closer to 5 the value $V1_i$ is, the more (larger or stronger) the characteristic represented by the characteristic value $F1_i$ is. This also applies to the value $V2_i$. Note that the values $V1_i$ and $V2_i$ the arbitrary characteristic values $F1_i$ and $F2_i$ take can be either continuous values or discrete values.

The method of calculating the first characteristic value in the above-described processing of step S104 will be described here.

For each of the first characteristic values $F1_1$ to $F1_{p-1}$ that are also commonly used as the second characteristic values, a characteristic value state $S_{ij}$ is obtained in accordance with a predetermined rule using the image feature calculated by the processing in step S103.

The characteristic value $F1_1$ in the table of FIG. 3 is "major axis". For example, the major axis (maximum diameter) of an ellipse obtained by approximating the boundary line of the abnormal shade region to an ellipse is calculated and obtained as the value $V1_1$.

A characteristic value $F1_2$ in the table of FIG. 3 is "irregularity of contour". For example, the value $V1_2$ (1 to 5) is calculated in accordance with the variance of the distances from the center of the abnormal shade to the respective points on the boundary line.

A characteristic value $F1_3$ in the table of FIG. 3 is "calcification". For example, the density histogram of the abnormal shade is created, and a value $V1_3$ is calculated in accordance with the ratio of density values within the density range corresponding to calcification. Similarly, a characteristic value $F1_4$ in the table of FIG. 3 is "gaseous portion". A value $V1_4$ is calculated using the density histogram.

On the other hand, for the characteristic values $F1_p$ to $F1_{q-1}$ that exist only as the first characteristic value, the image feature amount calculated in step S103 described above is directly used as the value $V1_i$.

As described above, in this embodiment, the first characteristic value calculation method is changed depending on the correspondence between the first characteristic value and the second characteristic value (for example, a first characteristic value corresponding to a second characteristic value exists, or the characteristic value exists only as the first characteristic value or the second characteristic value).

Figure 2:
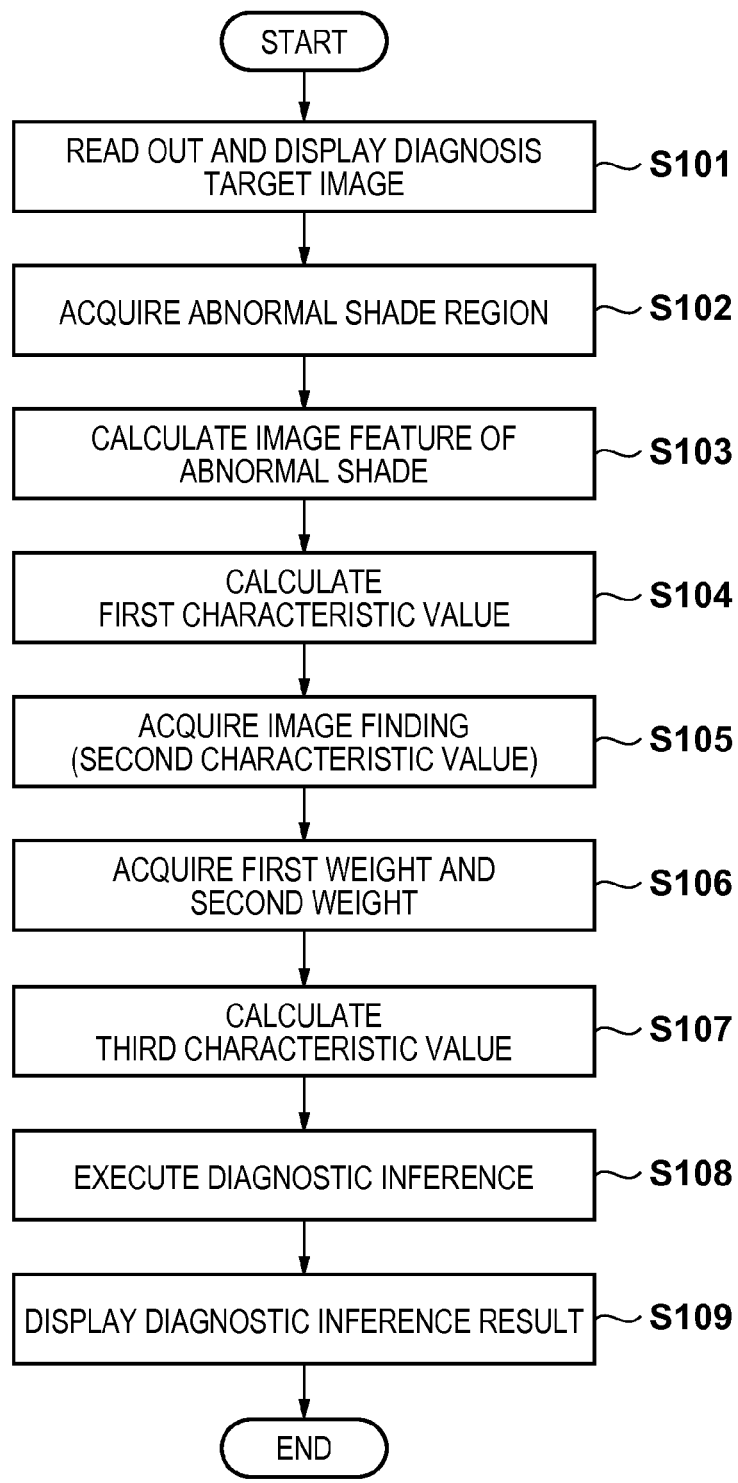
FIG. 2 is a flowchart showing an example of the procedure of processing of the image diagnosis assistance apparatus 10.

Referring back to the flowchart of FIG. 2, the weight acquisition unit 13 of the image diagnosis assistance apparatus 10 acquires the first weight for the first characteristic value and the second weight for the second characteristic value (step S106). The first weight and the second weight can have different values for the individual characteristic values. The method of calculating the first weight and the second weight will be described later.

The third characteristic value calculation unit 14 of the image diagnosis assistance apparatus 10 calculates a value $V3_i$ of the third characteristic value ($F3_i$, i=1 to n) by $$V3_i = (V1_i * W1_i + V2_i * W2_i)/(W1_i + W2_i) \quad (1)$$

(step S107). Note that if the values $V1_i$ and $V2_i$ are discrete values, the value $V3_i$ is also made discrete by making the value obtained by equation (1) discrete.

The inference unit 15 of the image diagnosis assistance apparatus 10 executes diagnostic inference (step S108). The diagnostic inference is performed using a known inference technique (Bayesian network, neural network, SVM, decision tree, or the like). When a probabilistic method such as Bayesian network is used as the inference technique, a likelihood is obtained for each of a plurality of image diagnosis names predetermined as a diagnostic inference result. When a discriminant method such as SVM is used as the inference technique, one image diagnosis name that is most probable as the diagnostic inference result is obtained.

Finally, the display processing unit 16 of the image diagnosis assistance apparatus 10 displays, on the display unit 36, the diagnostic inference result obtained by the processing in step S108 (step S109).

FIG. 4 is a table showing detailed examples of the first weight and the second weight for the first characteristic value and the second characteristic value exemplified in the table of FIG. 3.

In the table of FIG. 4, i is the index of the first characteristic value and the second characteristic value, $F1_i$ is the ith first characteristic value, and $F2_i$ is the ith second characteristic value. In addition, the first weight for the ith first characteristic value $F1_i$ is represented by $W1_i$, and the second weight for the ith second characteristic value $F2_i$ is represented by $W2_i$. In the example of the table shown in FIG. 4, the first weight $W1_i$ and the second weight $W2_i$ are set such that the sum of $W1_i$ and $W2_i$ becomes 1.0.

The methods of acquiring the above-described first weight $W1_i$ and second weight $W2_i$ can roughly be divided into two methods (first acquisition method and second acquisition method).

Although details will be described later, in the first acquisition method, the first weight $W1_i$ and the second weight $W2_i$ are predetermined by a statistical method, and a plurality of weight sets are stored in the storage unit 34. In the processing of step S106, one of the plurality of predetermined sets of the first weight $W1_i$ and second weight $W2_i$ is read out from the storage unit 34, thereby acquiring the first weight $W1_i$ and the second weight $W2_i$. Although details will be described later, in the second acquisition method, the first weight $W1_i$ and the second weight $W2_i$ are calculated for each diagnosis target image.

Figure 5:
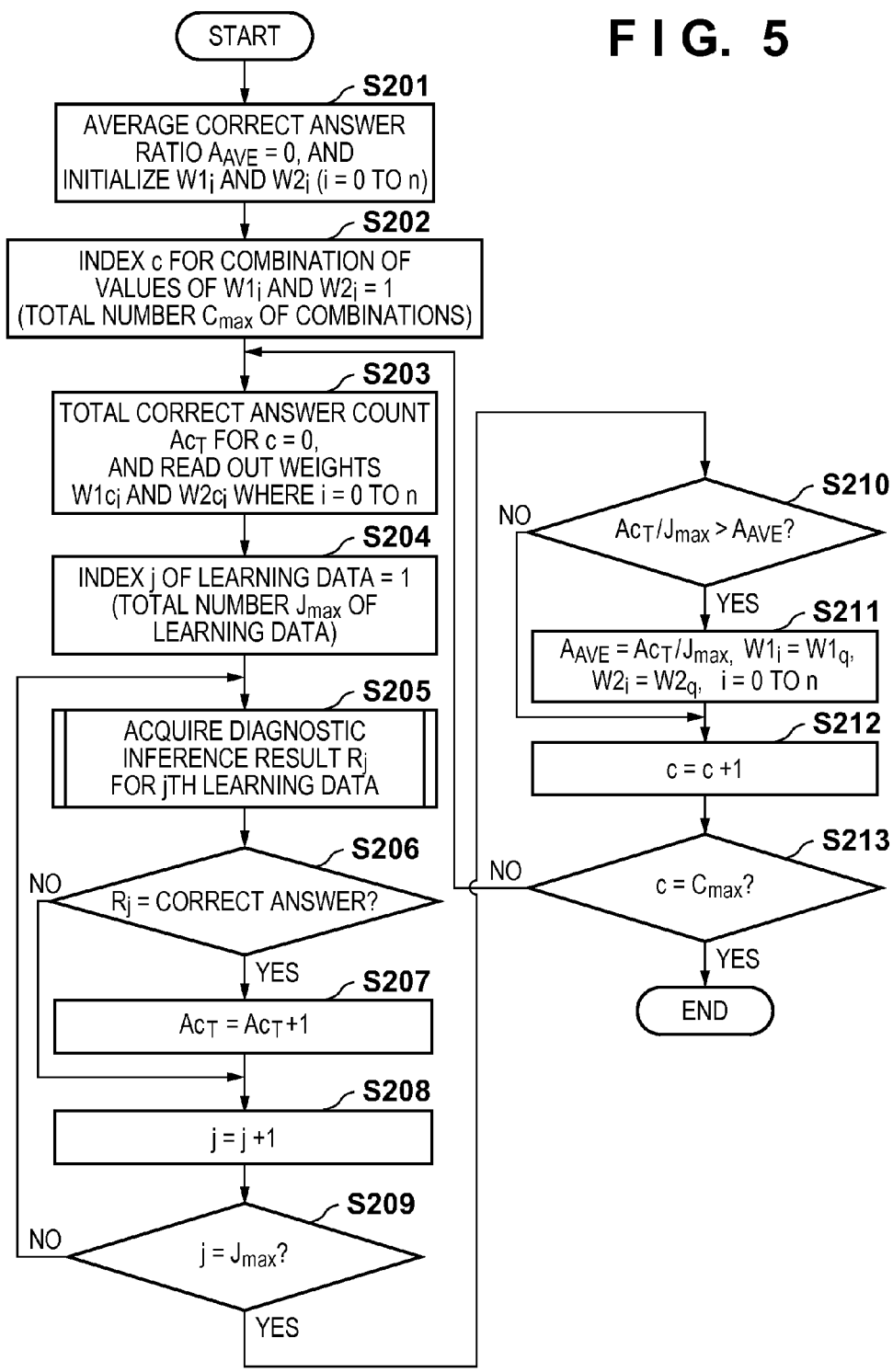
FIG. 5 is a flowchart showing an example of the procedure of processing of a first acquisition method (statistical method) of weights $W1_i$ and $W2_i$.

The first acquisition method (statistical method) of the weights $W1_i$ and $W2_i$ will be explained here with reference to FIG. 5. Note that when executing the processing shown in FIG. 5, it is necessary to prepare in advance a plurality of medical image data (learning data) for which the first characteristic values are already calculated, the second characteristic values are already input by the user, and the determined diagnosis names are already surveyed (correct diagnosis results are known).

In this processing, first, the weight acquisition unit 13 substitutes "0" into an average correct answer ratio $A_{AVE}$ and initializes the weights $W1_i$ and $W2_i$ (i=0 to n) (step S201). In the following processing, for example, assume that $W1_i$=0.0 and $W2_i$=1.0, although this does not depend on the initialization method.

Next, the weight acquisition unit 13 substitutes "1" into an index c of the combination of the values $W1_i$ and $W2_i$ (step S202). The total number of combinations (that is, the maximum value of c) will be expressed as $C_{max}$ hereinafter. Examples of the combinations of the weights $W1_i$ and $W2_i$ are $W1_1$=0.1 and $W2_1$=0.9, $W1_2$=0.0 and $W2_2$=1.0, ..., $W1_n$=0.0 and $W2_n$=1.0. There exist the weights $W1_i$ and $W2_i$ in various combinations satisfying $W1_i+W2_i$=1.0 for all indices i. Hence, the value of the index c is assigned to each combination and stored in the RAM 32.

The weight acquisition unit 13 also substitutes "0" into a total correct answer count $Ac_T$ for the index c and reads out a combination of weights $W1c_i$ and $W2c_i$ (i=0 to n) for the index c from the RAM 32 (step S203).

The weight acquisition unit 13 substitutes "1" into an index j of learning data (step S204). The total number of learning data (that is, the maximum value of j) will be expressed as $J_{max}$ hereinafter.

The weight acquisition unit 13 executes the above-described processing shown in FIG. 2 by setting the ith learning data as the diagnosis target image. A diagnostic inference result $R_j$ for the ith learning data is thus acquired (step S205).

The weight acquisition unit 13 determines whether the diagnostic inference result $R_j$ acquired by the processing in step S205 matches a known determined diagnosis name (correct diagnosis name) (that is, whether the diagnostic inference result is the correct answer) (step S206). If $R_j$ is the correct answer (YES in step S206), the weight acquisition unit 13 increments the total correct answer count $Ac_T$ by "1" (step S207) and increments the index j by "1" (step S208). On the other hand, if $R_j$ is wrong (NO in step S206), the weight acquisition unit 13 increments the index j by "1" (step S208).

After incrementing the index j, the weight acquisition unit 13 determines whether the index j has reached the maximum value $J_{max}$. If j has not reached $J_{max}$ (NO in step S209), the weight acquisition unit 13 returns to the processing in step S205 again.

If j has reached $J_{max}$ (YES in step S209), the weight acquisition unit 13 calculates a value (that is, the average correct answer ratio for the index c) by dividing the total correct answer count $Ac_T$ for the index c by the total number $J_{max}$ of learning data for the index c. The weight acquisition unit 13 determines whether the result is larger than the average correct answer ratio $A_{AVE}$ (step S210).

Upon determining that $Ac_T/J_{max}$ is not larger than $A_{AVE}$ (NO in step S210), the weight acquisition unit 13 increments the index c by "1" (step S212).

On the other hand, if $Ac_T/J_{max}$ is larger than $A_{AVE}$ (YES in step S210), the weight acquisition unit 13 substitutes the value $Ac_T/J_{max}$ into the average correct answer ratio $A_{AVE}$. The weight acquisition unit 13 also substitutes the values of the weights $W1c_i$ and $W2c_i$ for the index c into the values of the weights $W1_i$ and $W2_i$ (i=0 to n), respectively (step S211). After that, the weight acquisition unit 13 increments the index c by "1" (step S212).

After incrementing the index c, the weight acquisition unit 13 determines whether the index c has reached the maximum value $C_{max}$ (step S213). If c has not reached $C_{max}$ (NO in step S213), the weight acquisition unit 13 returns to the processing in step S203 again. On the other hand, if c has reached $C_{max}$, the weight acquisition unit 13 ends the processing.

With the above-described processing, the combination of the weights $W1_i$ and $W2_i$ (i=0 to n) with the highest average correct answer ratio $A_{AVE}$ for all learning data is obtained. However, if the value $V2_i$ of the ith second characteristic value $F2_i$ is not input by the user when actually executing step S106 shown in FIG. 2 for the diagnosis target image, the weights are set to $W1_i$=1.0 and $W2_i$=0.0.

The second acquisition method (method of calculating the weights each time) of the first weight $W1_i$ and the second weight $W2_i$ will be described next.

In the second acquisition method, the user inputs the plurality of second characteristic values ($F2_i$, i=1 to p−1, q to n) via the operation unit 35 and also inputs a user likelihood $S2_i$ for each second characteristic value. Note that the second characteristic value $F2_i$ and its likelihood $S2_i$ are acquired by the second characteristic value acquisition unit 12 in accordance with a user instruction from the operation unit 35.

When the input has ended, based on whether the likelihood $S2_i$ is larger than a predetermined threshold, the weight acquisition unit 13 reads out the values $W1_i$ and $W2_i$ stored in the storage unit 34 in advance for each case. For example, if the likelihood $S2_i$ is larger than the predetermined threshold, the weights are set to $W1_i$=0.0 and $W2_i$=1.0. If the likelihood $S2_i$ is smaller, the weights are set to $W1_i$=0.5 and $W2_i$=0.5. However, if the value $V2_i$ of the ith second characteristic value $F2_i$ is not input by the user, the weights are set to $W1_i$=1.0 and $W2_i$=0.0.

As described above, according to this embodiment, diagnosis assistance is performed using both the information of the first characteristic value calculated from the diagnosis target image and that of the second characteristic value input by the user. This allows provision of an apparatus usable in both the case in which the first characteristic value is calculated first and the case in which the second characteristic value is input first.

Using the first characteristic value, the second characteristic value, the correspondence between them, and the third characteristic value calculated using the first weight and the second weight enables performance of diagnostic inference more reliable than in a case in which one of the first characteristic value and the second characteristic value is used.

A representative embodiment of the present invention has been described above. However, the present invention is not limited to the embodiment illustrated and described above and changes and modifications can appropriately be made within the spirit and scope of the present invention.

For example, in the above embodiment, the arrangement that performs weighing has been described. However, the weighting need not always be performed. That is, even in an arrangement that does not perform weighing, it is possible to make an apparatus usable in both the case in which the first characteristic value is calculated first and the case in which the second characteristic value is input first.

According to the present invention, it is possible to obtain a diagnostic inference result more reliable than before.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-012433 filed on Jan. 24, 2012, which is hereby incorporated by reference herein in its entirety.

What is claimed is:

1. An apparatus for supporting diagnosis, comprising:
a region obtaining unit configured to obtain a region in a medical image;
a characteristic obtaining unit configured to obtain an image characteristic, the image characteristic being obtained from the obtained region in the medical image by processing the medical image;
a finding obtaining unit configured to obtain an image finding that is an assessment of the obtained region in the medical image, the image finding being based on an input to an operation unit for being operated by a user; and
a result obtaining unit configured to obtain an inference result from an inference unit having performed diagnostic inference based on the obtained image characteristic and the obtained image finding to output the inference result, wherein the obtained image characteristic and the obtained image finding are both obtained from the same obtained region in the medical image.

2. The apparatus according to claim 1, further comprising:
a weight acquisition unit configured to acquire a first weight and a second weight; and
a characteristic value calculation unit configured to calculate a third characteristic value based on a result obtained by weighting a first characteristic value corresponding to the image characteristic using the first weight and a result obtained by weighting a second characteristic value corresponding to the image finding using the second weight,
wherein the result obtaining unit obtains the inference result that is obtained by performing diagnostic inference for the obtained region in the medical image using the third characteristic value.

3. The apparatus according to claim 2, further comprising a storage unit configured to store a plurality of sets of the first weight and the second weight,
wherein the diagnostic inference is performed, using the plurality of sets of the weights, for a plurality of images whose diagnosis results are known, and the weight acquisition unit acquires a weight set with a highest correct answer ratio as the first weight and the second weight.

4. The apparatus according to claim 2, further comprising a storage unit configured to store a plurality of sets of the first weight and the second weight,
wherein the finding obtaining unit obtains a likelihood corresponding to the second characteristic value together with the second characteristic value based on the input to the operation unit for being operated by the user, and
if the likelihood is larger than a predetermined threshold, the weight acquisition unit acquires a set of the first weight and the second weight in which the second weight has a value larger than that of the first weight.

5. The apparatus according to claim 2, wherein if the finding obtaining unit cannot obtain the second characteristic value, the weight acquisition unit sets the second weight to 0.

6. The apparatus according to claim 2, wherein
$W1i$ is the first weight,
$W2i$ is the second weight,
$V1i$ is the first characteristic value,
$V2i$ is the second characteristic value,
$V3i$ is the third characteristic value, and
when $W1i+W2i=1.0$,
the characteristic value calculation unit calculates the third characteristic value by solving $$V3i=(V1i*W1i+V2i*W2i)/(W1i+W2i).$$

7. A processing method of an apparatus for supporting diagnosis, comprising:
obtaining a region in a medical image;
obtaining an image characteristic obtained from the obtained region in the medical image by processing the medical image;
obtaining an image finding that is an assessment of the obtained region in the medical image, the image finding being based on an input to an operation unit for being operated by a user; and
obtaining an inference result from an inference unit having performed diagnostic inference based on the obtained image characteristic and the obtained image finding to output the inference result, wherein the obtained image characteristic and the obtained image finding are both obtained from the same obtained region in the medical image.

8. A non-transitory computer-readable storage medium storing a computer program that causes a computer to function as:
a region obtaining unit configured to obtain a region in a medical image;
a characteristic obtaining unit configured to obtain an image characteristic obtained from the obtained region in the medical image by processing the medical image;
a finding obtaining unit configured to obtain an image finding that is an assessment of the obtained region in the medical image, the image finding being based on an input to an operation unit for being operated by a user; and
a result obtaining unit configured to obtain an inference result from an inference unit having performed diagnostic inference based on the obtained image characteristic and the obtained image finding to output the inference result, wherein the obtained image characteristic and the obtained image finding are both obtained from the same obtained region in the medical image.

9. An apparatus for supporting diagnosis, comprising:
a region obtaining unit configured to obtain a region in a medical image;
a first obtaining unit configured to obtain an image characteristic, the image characteristic being obtained from the obtained region in the medical image by processing the medical image;
a second obtaining unit configured to obtain an image finding of the obtained region, the image finding being based on an input to an operation unit for being operated by a user; and
an inference unit configured to, based on the obtained image characteristic and the obtained image finding, perform diagnostic inference for the obtained region in the medical image, in order to output an inference result for the obtained region, wherein the obtained image characteristic and the obtained image finding are both obtained from the same obtained region in the medical image.

10. An apparatus for supporting diagnosis, comprising:
a processor; and
a memory storing a program including instructions executed by the processor to perform a process comprising:
obtaining a region in a medical image;
obtaining an image characteristic, the image characteristic being obtained from the obtained region in the medical image by processing the medical image;
obtaining an image finding that is an assessment of the obtained region in the medical image, the image finding being based on an input to an operation unit for being operated by a user; and
obtaining an inference result from an inference unit having performed diagnostic inference based on the obtained image characteristic and the obtained image finding to output the inference result, wherein the obtained image characteristic and the obtained image finding are both obtained from the same obtained region in the medical image.

11. An apparatus for supporting diagnosis, comprising:
a processor; and
a memory storing a program including instructions executed by the processor to perform a process comprising:

obtaining a region in a medical image;
obtaining an image characteristic, the image characteristic being obtained from the obtained region in the medical image by processing the medical image;
obtaining an image finding of the obtained region, the image finding being based on an input to an operation unit for being operated by a user; and
performing, based on the obtained image characteristic and the obtained image finding, diagnostic inference for the obtained region in the medical image, in order to output an inference result for the obtained region, wherein the obtained image characteristic and the obtained image finding are both obtained from the same obtained region in the medical image.

12. A method for supporting diagnosis, comprising:
obtaining a region in a medical image;
obtaining an image characteristic, the image characteristic obtained from the obtained region in the medical image by processing the medical image;
obtaining an image finding of the obtained region, the image finding based on an input to an operation unit for being operated by a user; and
performing, based on the obtained image characteristic and the obtained image finding, diagnostic inference for the obtained region in the medical image, in order to output an inference result for the obtained region, wherein the obtained image characteristic and the obtained image finding are both obtained from the same obtained region in the medical image.

13. An image diagnosis assistance apparatus comprising:
a first characteristic value calculation unit configured to calculate a first characteristic value based on an image feature of an image that is a diagnosis target;
a second characteristic value acquisition unit configured to acquire a second characteristic value based on findings information of the image input by a user via an operation unit;
an inference unit configured to perform diagnostic inference for the image based on the first characteristic value, the second characteristic value, and a reliability of inference of the first characteristic value and the second characteristic value;
a weight acquisition unit configured to acquire a first weight and a second weight;
a third characteristic value calculation unit configured to calculate a third characteristic value based on a result obtained by weighting the first characteristic value using the first weight and a result obtained by weighting the second characteristic value using the second weight; and
a storage unit configured to store a plurality of sets of the first weight and the second weight,
wherein the inference unit performs diagnostic inference for a predetermined region of the image using the third characteristic value,
wherein the second characteristic value acquisition unit acquires a likelihood corresponding to the second characteristic value together with the second characteristic value based on the findings information input by the user via the operation unit, and
wherein if the likelihood is larger than a predetermined threshold, the weight acquisition unit acquires a set of the first weight and the second weight in which the second weight has a value larger than that of the first weight.

14. A processing method of an image diagnosis assistance apparatus, comprising:
calculating, by a first characteristic value calculation unit, a first characteristic value based on an image feature of an image that is a diagnosis target;
acquiring, by a second characteristic value acquisition unit, a second characteristic value based on findings information of the image input by a user via an operation unit;
acquiring, by a weight acquisition unit, a first weight and a second weight;
storing, by a storage unit, a plurality of sets of the first weight and the second weight;
calculating, by a third characteristic value calculation unit, a third characteristic value based on a result obtained by weighting the first characteristic value using the first weight and a result obtained by weighting the second characteristic value using the second weight; and
performing, by an inference unit, diagnostic inference for the image based on the first characteristic value, the second characteristic value, and a reliability of inference of the first characteristic value and the second characteristic value,
wherein the inference unit performs diagnostic inference for a predetermined region of the image using the third characteristic value,
wherein the second characteristic value acquisition unit acquires a likelihood corresponding to the second characteristic value together with the second characteristic value based on the findings information input by the user via the operation unit, and
wherein if the likelihood is larger than a predetermined threshold, the weight acquisition unit acquires a set of the first weight and the second weight in which the second weight has a value larger than that of the first weight.

15. A non-transitory computer-readable storage medium storing a computer program that causes a computer to function as:
a first characteristic value calculation unit configured to calculate a first characteristic value based on an image feature of an image that is a diagnosis target;
a second characteristic value acquisition unit configured to acquire a second characteristic value based on findings information of the image input by a user via an operation unit;
an inference unit configured to perform diagnostic inference for the image based on the first characteristic value, the second characteristic value, and a reliability of inference of the first characteristic value and the second characteristic value;
a weight acquisition unit configured to acquire a first weight and a second weight;
a third characteristic value calculation unit configured to calculate a third characteristic value based on a result obtained by weighting the first characteristic value using the first weight and a result obtained by weighting the second characteristic value using the second weight; and
a storage unit configured to store a plurality of sets of the first weight and the second weight,
wherein the inference unit performs diagnostic inference for a predetermined region of the image using the third characteristic value,
wherein the second characteristic value acquisition unit acquires a likelihood corresponding to the second characteristic value together with the second characteristic value based on the findings information input by the user via the operation unit, and wherein if the likelihood is larger than a predetermined threshold, the weight acquisition unit acquires a set of the first weight and the second weight in which the second weight has a value larger than that of the first weight.

16. An image diagnosis assistance apparatus comprising:
a first characteristic value calculation unit configured to calculate a first characteristic value based on an image feature of an image that is a diagnosis target;
a second characteristic value acquisition unit configured to acquire a second characteristic value based on findings information of the image input by a user via an operation unit;
an inference unit configured to perform diagnostic inference for the image based on the first characteristic value, the second characteristic value, and a reliability of inference of the first characteristic value and the second characteristic value;
a weight acquisition unit configured to acquire a first weight and a second weight; and
a third characteristic value calculation unit configured to calculate a third characteristic value based on a result obtained by weighting the first characteristic value using the first weight and a result obtained by weighting the second characteristic value using the second weight,
wherein the inference unit performs diagnostic inference for a predetermined region of the image using the third characteristic value, and
wherein
$W1i$ is the first weight,
$W2i$ is the second weight,
$V1i$ is the first characteristic value,
$V2i$ is the second characteristic value,
$V3i$ is the third characteristic value, and
when $W1i+W2i=1.0$,
the third characteristic value calculation unit calculates the third characteristic value by solving $$V3i=(V1i*W1i+V2i*W2i)/(W1i+W2i).$$

17. A processing method of an image diagnosis assistance apparatus, comprising:
calculating, by a first characteristic value calculation unit, a first characteristic value based on an image feature of an image that is a diagnosis target;
acquiring, by a second characteristic value acquisition unit, a second characteristic value based on findings information of the image input by a user via an operation unit;
acquiring, by a weight acquisition unit, a first weight and a second weight;
calculating, by a third characteristic value calculation unit, a third characteristic value based on a result obtained by weighting the first characteristic value using the first weight and a result obtained by weighting the second characteristic value using the second weight; and
performing, by an inference unit, diagnostic inference for the image based on the first characteristic value, the second characteristic value, and a reliability of inference of the first characteristic value and the second characteristic value,
wherein the inference unit performs diagnostic inference for a predetermined region of the image using the third characteristic value, and wherein
$W1i$ is the first weight,
$W2i$ is the second weight,
$V1i$ is the first characteristic value,
$V2i$ is the second characteristic value,
$V3i$ is the third characteristic value, and
when $W1i+W2i=1.0$,
the third characteristic value calculation unit calculates the third characteristic value by solving $$V3i=(V1i*W1i+V2i*W2i)/(W1i+W2i).$$

18. A non-transitory computer-readable storage medium storing a computer program that causes a computer to function as:
a first characteristic value calculation unit configured to calculate a first characteristic value based on an image feature of an image that is a diagnosis target;
a second characteristic value acquisition unit configured to acquire a second characteristic value based on findings information of the image input by a user via an operation unit;
an inference unit configured to perform diagnostic inference for the image based on the first characteristic value, the second characteristic value, and a reliability of inference of the first characteristic value and the second characteristic value;
a weight acquisition unit configured to acquire a first weight and a second weight; and
a third characteristic value calculation unit configured to calculate a third characteristic value based on a result obtained by weighting the first characteristic value using the first weight and a result obtained by weighting the second characteristic value using the second weight,
wherein the inference unit performs diagnostic inference for a predetermined region of the image using the third characteristic value, and
wherein
$W1i$ is the first weight,
$W2i$ is the second weight,
$V1i$ is the first characteristic value,
$V2i$ is the second characteristic value,
$V3i$ is the third characteristic value, and
when $W1i+W2i=1.0$,
the third characteristic value calculation unit calculates the third characteristic value by solving $$V3i=(V1i*W1i+V2i*W2i)/(W1i+W2i).$$

19. An apparatus for supporting diagnosis, comprising:
a region obtaining unit configured to obtain a region in a medical image;
a characteristic obtaining unit configured to obtain an image characteristic, the image characteristic being obtained from the obtained region in the medical image by processing the medical image;
a finding obtaining unit configured to obtain an image finding that is an assessment of the obtained region in the medical image, the image finding being based on an input to an operation unit for being operated by a user;
a weight acquisition unit configured to acquire a first weight and a second weight;
a storage unit configured to store a plurality of sets of the first weight and the second weight;
a characteristic value calculation unit configured to calculate a third characteristic value based on a result obtained by weighting a first characteristic value corresponding to the image characteristic using the first weight and a result obtained by weighting a second characteristic value corresponding to the image finding using the second weight; and a result obtaining unit configured to obtain an inference result from an inference unit having performed diagnostic inference based on the obtained image characteristic and the obtained image finding to output the inference result, wherein the result obtaining unit obtains the inference result that is obtained by performing diagnostic inference for the obtained region in the medical image using the third characteristic value, and wherein the diagnostic inference is performed, using the plurality of sets of the first weight and the second weight, for a plurality of images whose diagnosis results are known, and the weight acquisition unit acquires a weight set with a highest correct answer ratio as the first weight and the second weight.

20. A processing method of an apparatus for supporting diagnosis, comprising:

obtaining a region in a medical image;

obtaining an image characteristic obtained from the obtained region in the medical image by processing the medical image;

obtaining an image finding that is an assessment of the obtained region in the medical image, the image finding being based on an input to an operation unit for being operated by a user;

acquiring a first weight and a second weight;

storing a plurality of sets of the first weight and the second weight;

calculating a third characteristic value based on a result obtained by weighting a first characteristic value corresponding to the image characteristic using the first weight and a result obtained by weighting a second characteristic value corresponding to the image finding using the second weight; and obtaining an inference result from an inference unit having performed diagnostic inference based on the obtained image characteristic and the obtained image finding to output the inference result, wherein the inference result is obtained by performing diagnostic inference for the obtained region in the medical image using the third characteristic value, and wherein the diagnostic inference is performed, using the plurality of sets of the first weight and the second weight, for a plurality of images whose diagnosis results are known, and a weight set with a highest correct answer ratio is acquired as the first weight and the second weight.

21. A non-transitory computer-readable storage medium storing a computer program that causes a computer to function as a region obtaining unit configured to obtain a region in a medical image;

a characteristic obtaining unit configured to obtain an image characteristic obtained from the obtained region in the medical image by processing the medical image;

a finding obtaining unit configured to obtain an image finding that is an assessment of the obtained region in the medical image, the image finding being based on an input to an operation unit for being operated by a user;

a weight acquisition unit configured to acquire a first weight and a second weight;

a storage unit configured to store a plurality of sets of the first weight and the second weight;

a characteristic value calculation unit configured to calculate a third characteristic value based on a result obtained by weighting a first characteristic value corresponding to the image characteristic using the first weight and a result obtained by weighting a second characteristic value corresponding to the image finding using the second weight; and a result obtaining unit configured to obtain an inference result from an inference unit having performed diagnostic inference based on the obtained image characteristic and the obtained image finding to output the inference result, wherein the result obtaining unit obtains the inference result that is obtained by performing diagnostic inference for the obtained region in the medical image using the third characteristic value, and wherein the diagnostic inference is performed, using the plurality of sets of the first weight and the second weight, for a plurality of images whose diagnosis results are known, and the weight acquisition unit acquires a weight set with a highest correct answer ratio as the first weight and the second weight.

* * * * *